US008568396B2

(12) United States Patent
Bourne (10) Patent No.: US 8,568,396 B2
(45) Date of Patent: Oct. 29, 2013

(54) FLOODED LIQUEFACTION HAND PIECE ENGINE (75) Inventor: John Morgan Bourne, Irvine, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 851 days.

(21) Appl. No.: 12/724,773

(22) Filed: Mar. 16, 2010

(65) Prior Publication Data

US 2011/0144632 A1 Jun. 16, 2011

Related U.S. Application Data (60) Provisional application No. 61/285,246, filed on Dec. 10, 2009.

(51) Int. Cl.
*A61B 18/04* (2006.01)

(52) U.S. Cl.
USPC .......................................................... 606/27

(58) Field of Classification Search
USPC .......................................... 606/27, 34, 39, 41
See application file for complete search history.

(56) References Cited

U.S. PATENT DOCUMENTS

| | | | |
|---|---|---|---|
| 4,808,154 A | 2/1989 | Freeman | |
| 5,413,556 A | 5/1995 | Whittingham | |
| 5,989,212 A | 11/1999 | Sussman et al. | |
| 5,997,499 A | 12/1999 | Sussman et al. | |
| 6,080,128 A | 6/2000 | Sussman et al. | |
| 6,110,162 A | 8/2000 | Sussman et al. | |
| 6,179,805 B1 | 1/2001 | Sussman et al. | |
| 6,196,989 B1 | 3/2001 | Padget et al. | |
| 6,206,848 B1 | 3/2001 | Sussman et al. | |
| 6,287,274 B1 | 9/2001 | Sussman et al. | |
| 6,315,755 B1 | 11/2001 | Sussman | |
| 6,331,171 B1 | 12/2001 | Cohen | |
| 6,398,759 B1 | 6/2002 | Sussman et al. | |
| 6,575,929 B2 | 6/2003 | Sussman et al. | |
| 6,579,270 B2 | 6/2003 | Sussman et al. | |

(Continued)

FOREIGN PATENT DOCUMENTS

| | | |
|---|---|---|
| DE | 19804065 A1 | 12/1999 |
| DE | 102007031618 B3 | 12/2008 |

(Continued)

OTHER PUBLICATIONS

International Searching Authority, International Search Report, PCT/US2010/055217, Feb. 24, 2011, 4 pages.

(Continued)

*Primary Examiner* — Michael Peffley
*Assistant Examiner* — Daniel Fowler (57) ABSTRACT In various embodiments, an ophthalmic handpiece may include a handpiece body with a pulse chamber and flooded engine compartment configured to receive fluid from a surgical console through a fluid inlet port. Heated pulses from the pulse chamber and cooler fluid from the flooded engine compartment may flow through a tip into the eye. In some embodiments, the tip may be a dual lumen tip that keeps the flows from the pulse chamber and flooded engine compartment separate until they exit the tip. In some embodiments, a tip, coupled to a merging chamber where the flows may merge prior to the tip, may be a single lumen tip that directs the heated pulses and irrigation fluid simultaneously to a lens to liquefy the lens for removal from the eye.

16 Claims, 8 Drawing Sheets

(56) References Cited

U.S. PATENT DOCUMENTS

| | | |
|---|---|---|
| 6,589,201 B1 | 7/2003 | Sussman et al. |
| 6,589,204 B1 | 7/2003 | Sussman et al. |
| 6,648,847 B2 | 11/2003 | Sussman et al. |
| 6,676,628 B2 | 1/2004 | Sussman et al. |
| 6,852,093 B1 | 2/2005 | Boukhny |
| 6,860,868 B1 | 3/2005 | Sussman et al. |
| 6,921,385 B2 | 7/2005 | Clements et al. |
| 7,276,060 B2 | 10/2007 | Madden |
| 7,758,585 B2 | 7/2010 | Sussman et al. |
| 2002/0161326 A1 | 10/2002 | Sussman et al. |
| 2005/0038417 A1 | 2/2005 | Ghannoum et al. |
| 2005/0192566 A1* | 9/2005 | Madden .................. 606/27 |
| 2006/0058823 A1 | 3/2006 | Dimalanta et al. |
| 2006/0161101 A1 | 7/2006 | Dimalanta et al. |
| 2006/0184091 A1 | 8/2006 | Dimalanta et al. |
| 2006/0212037 A1 | 9/2006 | Sussman et al. |
| 2006/0224116 A1 | 10/2006 | Underwood et al. |

FOREIGN PATENT DOCUMENTS

| | | |
|---|---|---|
| EP | 1199054 A1 | 4/2002 |
| EP | 1199504 B1 | 5/2004 |
| WO | WO 2006/101727 A2 | 9/2006 |
| WO | WO 2006/101727 A3 | 9/2007 |
| WO | WO 2010/036610 A1 | 4/2010 |
| WO | WO 2011/07161 A1 | 6/2011 |

OTHER PUBLICATIONS

International Searching Authority, Written Opinion of the International Searching Authority, PCT/US2010/055217, Feb. 24, 2011, 7 pages.

* cited by examiner

FLOODED LIQUEFACTION HAND PIECE ENGINE

PRIORITY CLAIM

This application claims the benefit of priority of U.S. Provisional Patent Application Ser. No. 61/285,246 titled "Flooded Liquefaction Hand Piece Engine", filed on Dec. 10, 2009, whose inventors are John Morgan Bourne and Daniel J. Kao, which is hereby incorporated by reference in its entirety as though fully and completely set forth herein.

FIELD OF THE INVENTION

The present invention generally pertains to cataract surgery. More particularly, but not by way of limitation, the present invention pertains to a liquefaction hand piece engine.

DESCRIPTION OF THE RELATED ART

The human eye in its simplest terms functions to provide vision by transmitting light through a clear outer portion called the cornea, and focusing the image by way of the lens onto the retina. The quality of the focused image depends on many factors including the size and shape of the eye, and the transparency of the cornea and lens.

When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an artificial intraocular lens (IOL).

One cataract removal technique involves the injection of hot water or saline to liquefy or gellate the hard lens nucleus, thereby making it possible to aspirate the liquefied lens from the eye. Aspiration may be conducted with the injection of the heated solution and the injection of a relatively cool solution, thereby quickly cooling and removing the heated solution.

SUMMARY

In various embodiments, an ophthalmic handpiece configured to direct heated pulses at a lens to liquefy the lens for removal from the eye may include a handpiece body configured to receive fluid through a fluid inlet port from a surgical console and a pulse chamber and a flooded engine compartment configured to receive fluid from the fluid inlet port. The pulse chamber may be bounded by a pair of electrodes configured to deliver a current to a fluid in the pulse chamber to cause the fluid to boil and exit the pulse chamber (a check valve in the handpiece may inhibit fluid flow from the pulse chamber toward the fluid inlet port). In some embodiments, the flooded engine compartment may surround the exterior of the pulse chamber and be in thermal contact with the pulse chamber such that fluid in the flooded engine compartment may remove heat from the pulse chamber. In some embodiments, heated pulses from the pulse chamber and cooler fluid from the flooded engine compartment may flow through a tip into the eye. In some embodiments, the tip may be a dual lumen tip that keeps the flows from the pulse chamber and flooded engine compartment separate until they exit the tip.

In some embodiments, heated pulses from the pulse chamber and fluid from the flooded engine compartment may flow into a merging chamber where heated pulses from the pulse chamber and the fluid from the flooded engine compartment may mix (e.g., such that a temperature of the mixed fluid may be between a temperature of the heated fluid from the pulse chamber and a temperature of the fluid from the flooded engine compartment). In some embodiments, a tip, coupled to the merging chamber, may be a single lumen tip that provides the heated pulses, from the pulse chamber, and irrigation fluid, from the flooded engine compartment, simultaneously to a lens to liquefy the lens for removal from the eye. During an initial priming process, fluid may flow through the flooded engine compartment, the merging chamber, and then into the pulse chamber before current is directed to fluid in the pulse chamber. Further, the check valve may be wetted by the fluid flow from the fluid inlet port to the flooded engine compartment such that if the check valve were stuck due to a salt bond, the check valve may become unstuck via the wetting.

BRIEF DESCRIPTION OF THE DRAWINGS

For a more complete understanding of the present invention, reference is made to the following description taken in conjunction with the accompanying drawings in which.

It is to be understood that both the foregoing general description and the following detailed description are exemplary and explanatory only and are intended to provide a further explanation of the present invention as claimed.

DETAILED DESCRIPTION OF THE EMBODIMENTS

Figure 1:
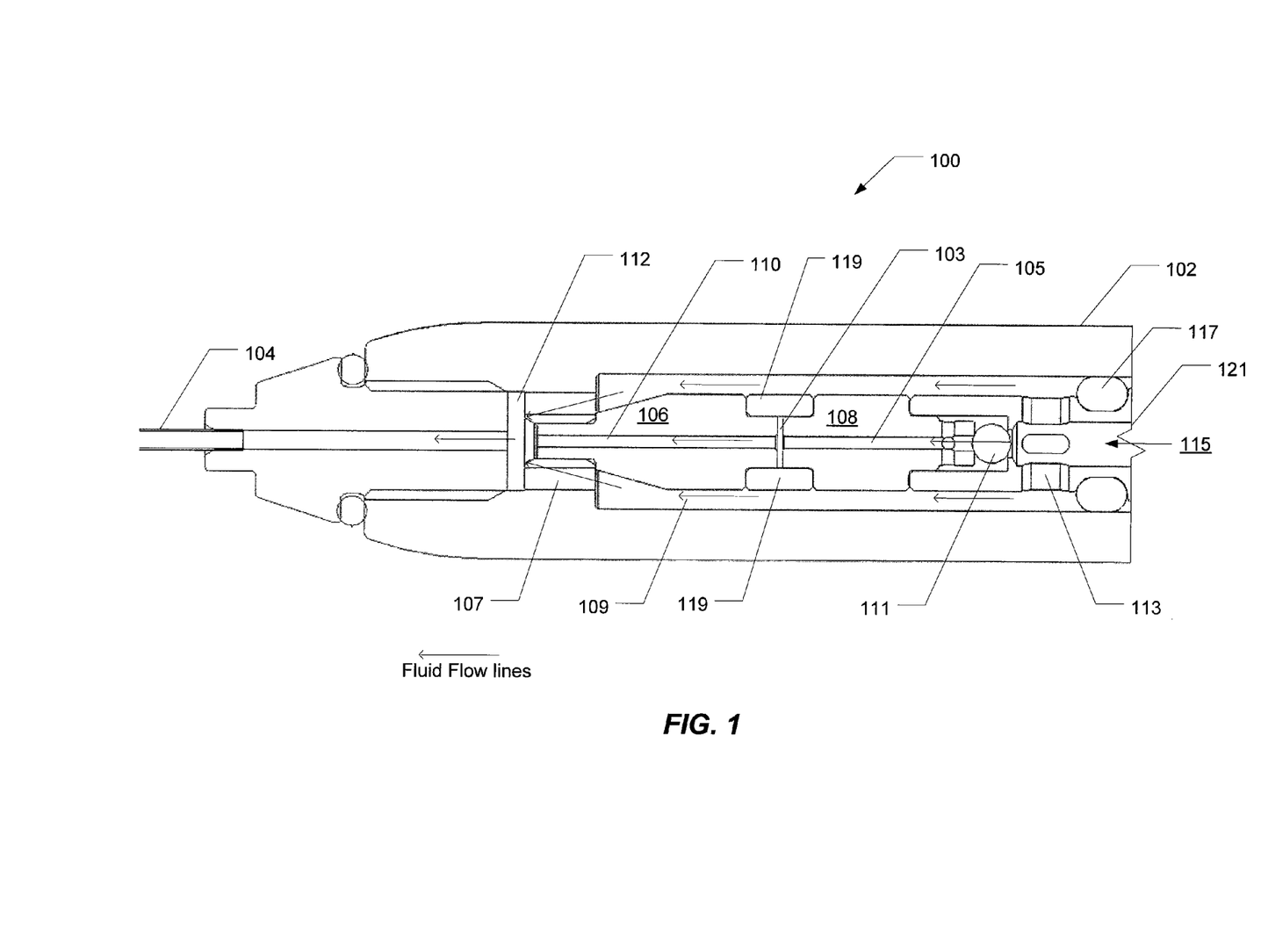
FIG. 1 is a side cross-sectional view of a handpiece, according to an embodiment.
Figure 2:
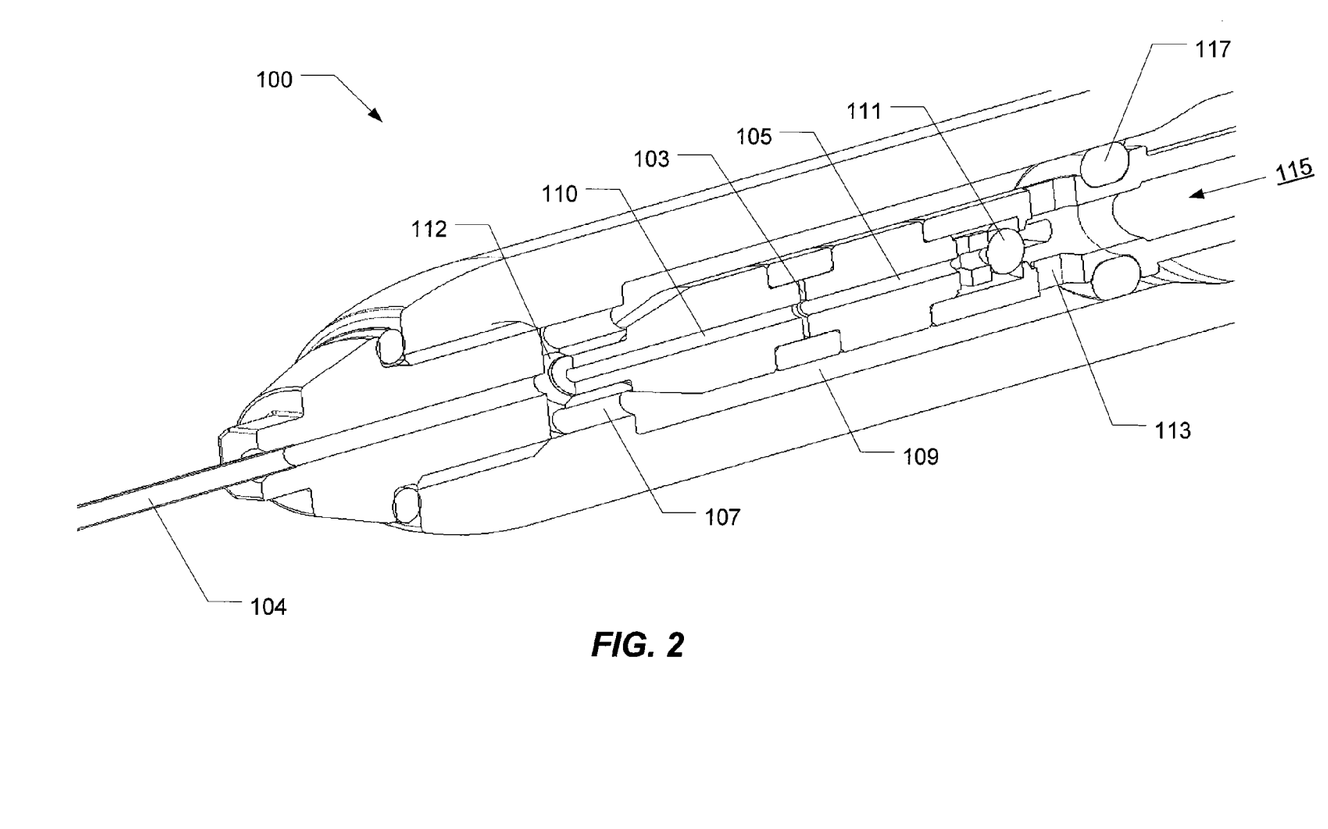
FIG. 2 is an isometric cross-sectional view of the handpiece, according to an embodiment.

As seen in FIGS. 1-2, handpiece 100 may include a handpiece body 102 with an operative tip 104. The hand piece body 102 may include a pulse chamber 103, pulse pathways 105/110, irrigation pathway 107, flooded engine compartment 109, check valve 111, and irrigation port 113. A fluid source 115 may couple to one end of the hand piece body 102 (e.g., tubing from a surgical console may deliver fluid to a fluid inlet port 121 on the hand piece 100). In some embodiments, body 102 may be made from plastic, titanium, or stainless steel (other materials are also possible). As seen in FIG. 1, pulse chamber 103 may be sealed on both sides by electrodes 106 and 108. Surgical fluid (e.g., saline irrigating solution) from the fluid source 115 may enter the pulse chamber 103 from the inlet pulse pathway 105 after passing through the check valve 111. Electrical current from the electrodes 106 and 108 may travel through the surgical fluid causing it to boil (electrical current may be provided, for example, from a surgical console to the handpiece 100 through a power cable). The surgical fluid may then expand rapidly out of the pulse chamber 103 and into the exit pulse pathway 110. The electrode current may be pulsed or continuous. The magnitude and/or frequency of the current pulses may be varied (e.g., through user input) to control the temperature, speed, and magnitude of the fluid pulses leaving the pulse chamber 103. The check valve 111 may prevent the expanding fluid from exiting the opposing end of the handpiece (toward the fluid source 115). An insulated spacer ring 119 may secure and space the electrodes 106 and 108.

In some embodiments, in addition to the surgical fluid from the fluid source 115 entering the inlet pulse pathway 105, surgical fluid may also enter the flooded engine compartment 109 around the exterior of the electrodes 106 and 108. The surgical fluid may flow through the flooded engine compartment 109 and through the irrigation pathway 107 and recombine with the surgical fluid pulse (exiting from the pulse chamber 103) in a merging chamber 112 that joins the irrigation pathway 107 and the exit pulse pathway 112. As seen in FIG. 4b, in some embodiments, the flows may not recombine in a merging chamber 112, but may instead recombine in the eye after exiting a dual lumen tip 415. The surgical fluid flowing through the flooded engine compartment 109 may provide cooling to the engine (which may include the electrodes 106/108 and pulse chamber 103) by absorbing excess heat from the boiling of the surgical fluid in the pulse chamber 103. In some embodiments, the electrodes 106/108 may be electrically insulated (e.g., by an insulating coating or insulated wrap) to prevent current from entering the surgical fluid in the flooded engine compartment 109. An O-ring 117 (e.g., made out of an elastomer) may seal the opposing end of the flooded engine compartment 109. Other structures for sealing the compartment may also be used. The fluid pulse from the pulse chamber 103 and the fluid from the flooded engine compartment 109 may be delivered through a tip 104 (which may be, for example, a single lumen tip or a dual lumen tip). In some embodiments, the single lumen tip 104 may provide both irrigation and fluidic pulses simultaneously through the same fluid pathway. The single lumen may increase the flow available per a given tip diameter (e.g., eliminating a separate, inner lumen may increase the cross-sectional area of the total fluid pathway which may reduce an amount of surface contact between the fluid lumen(s) and an eye). The heated, pulsed fluid exiting the tip 104 may be useful, for example, in removing residual cataract debris inside a capsular bag of the eye post-lens nucleus removal. Other uses of the heated/pulsed fluid are also possible.

At the start of a procedure, as the surgical fluid first flows into the handpiece 100 through port 121, the surgical fluid may flow through the check valve 111 and into the pulse chamber 103. The surgical fluid may also flow through the flooded engine compartment 109, into the exit pulse pathway 112 and then back into the pulse chamber 103. Both fluid flows may act to prime the pulse chamber 103 (in some embodiments, the pulse chamber 103 may thus be primed before current is supplied to the electrodes 106/108). Because the fluid pathways may split at the check valve 111, the fluid flowing through irrigation port 113 into the flooded engine compartment 109 may provide a vented fluid pathway for fluid to wet the check valve 111. If the check valve 111 was stuck due to a salt bond, the wetting of the check valve 111 (from fluid flowing through the irrigation port 113) may break the salt bond to allow fluid to flow past the check valve 111 and into the pulse chamber 103. When the electrodes 106/108 are subsequently charged, the fluid pulses leaving the exit pulse pathway 112 may inhibit backward flow of fluid through the exit pulse pathway 112 and may propel the fluid (from the fluid pulse and from flooded engine compartment 109) into the tip 104. In some embodiments, the cooler fluid from the flooded engine compartment 109 may cool the heated fluid from the pulse chamber 103 as the two fluids merge in the merging chamber 112.

In addition to improved priming, the proximity of the fluid pathways (e.g., the irrigation pathway through the flooded engine compartment 109 may be in contact with the engine providing the pulse pathway through the pulse chamber 103) may provide for embodiments of the handpiece with smaller outer handpiece body profiles than handpieces with distinctly separated irrigation fluid and pulse pathways (entirely separated pathways may require more handpiece volume).

Figure 3:
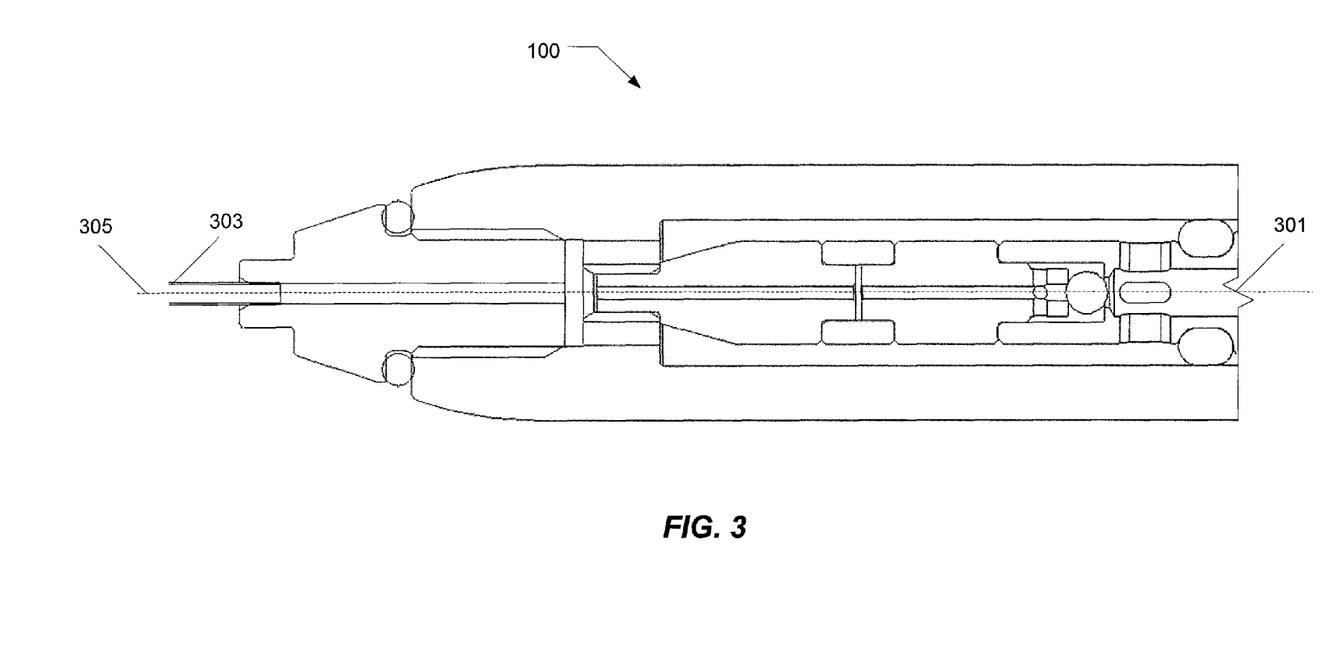
FIG. 3 illustrates a centerline of the handpiece, according to an embodiment.

As seen in FIG. 3, in some embodiments, momentum of the fluidic pulses through the handpiece 101 may be maintained by alignment of the inlet 301 and exit 303 along a straight line 305. For example, the pulsed pathway may not have bends or curves that may absorb energy from the pulsed fluid. Other pathway configurations are also contemplated.

Figure 4A:
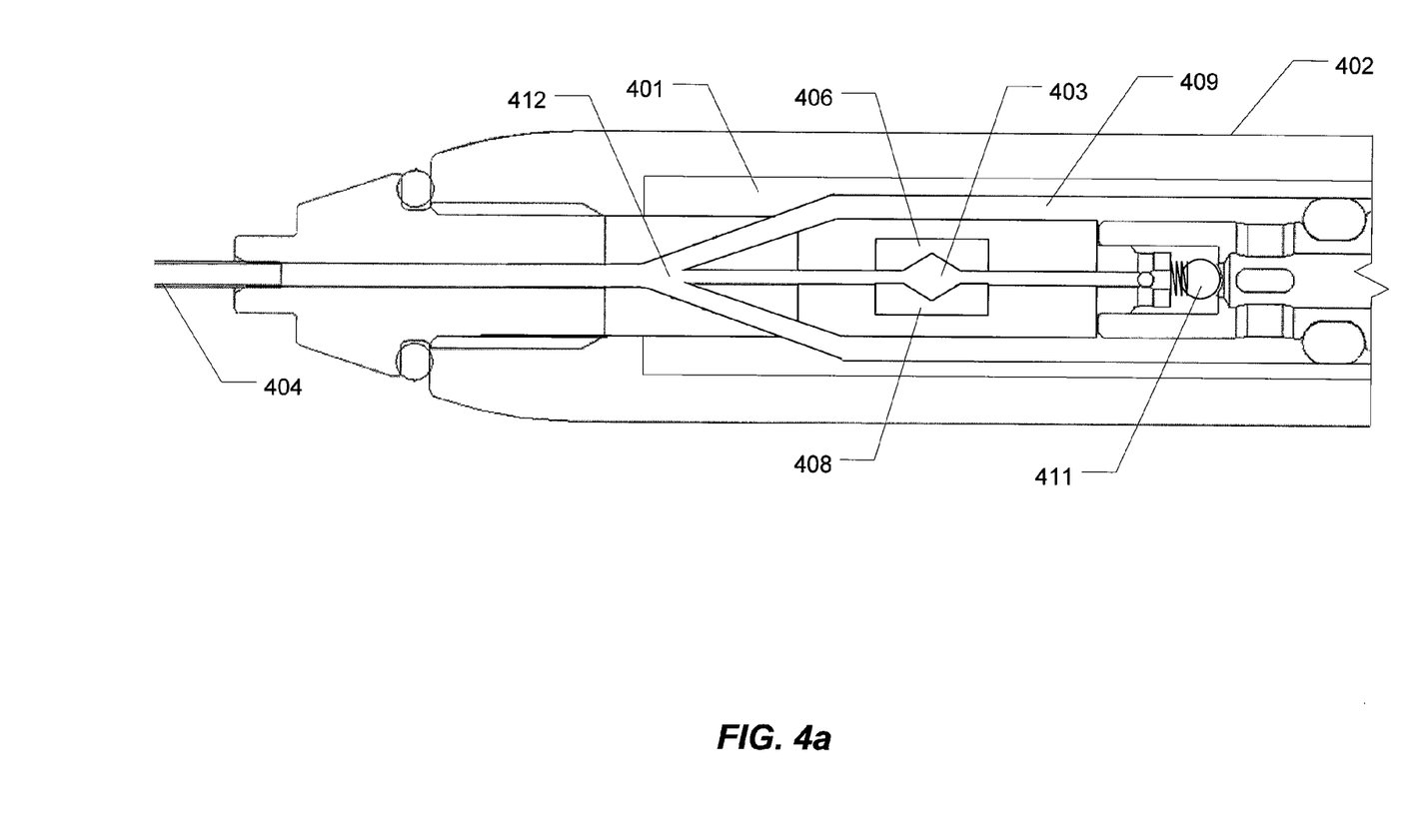
FIGS. 4a-c illustrate a side cross-sectional view of additional embodiments of the handpiece.
Figure 4B:
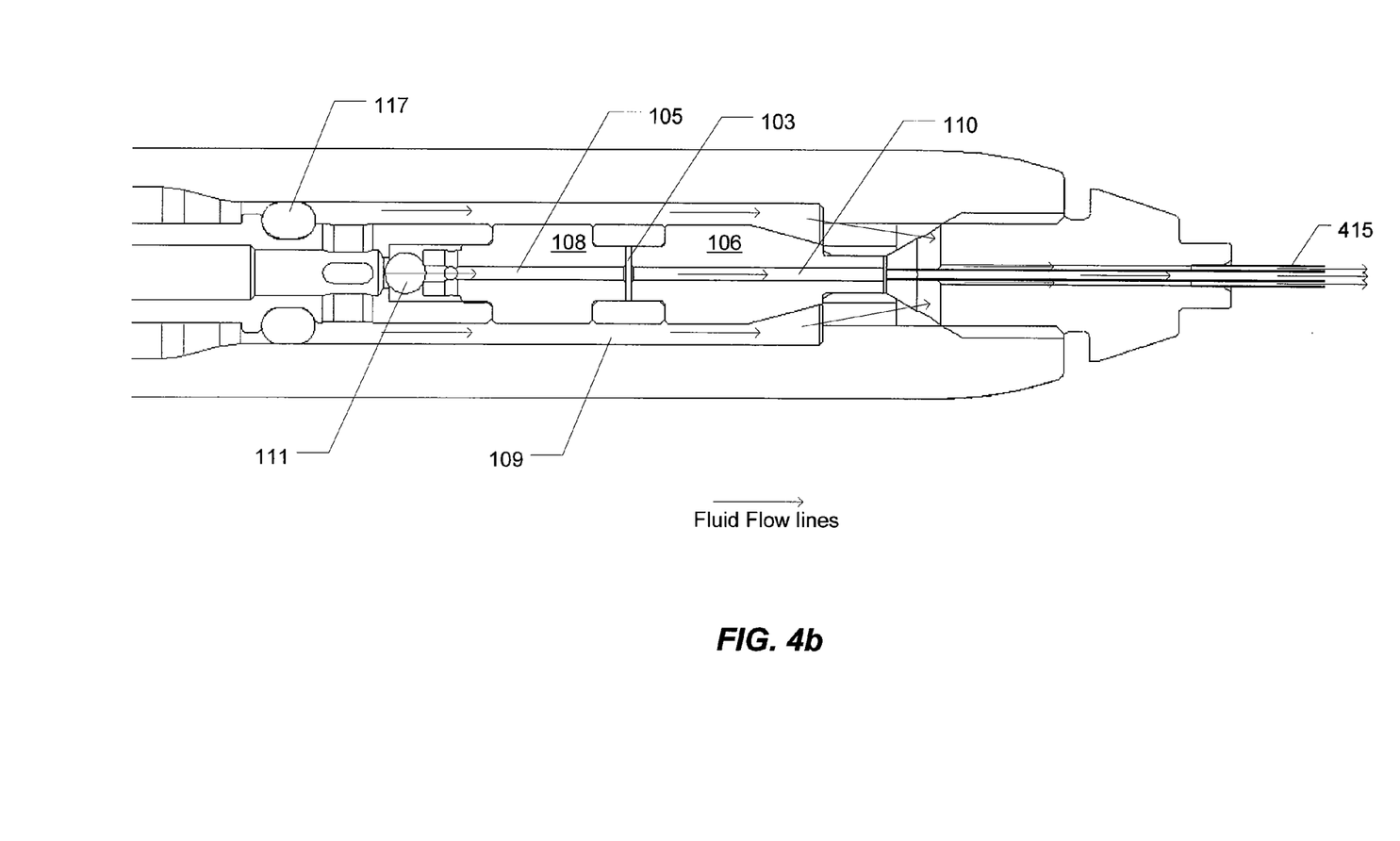

FIG. 4a illustrates an alternate embodiment of the handpiece. As seen in FIG. 4a, the hand piece body 402 may include pulse chamber 403 with electrodes 406/408, flooded engine compartment 409, merge chamber 412, check valve 411, and tip 404. As seen in FIG. 4a, the electrodes 406/408 may be located above and below the pulse chamber 403. In some embodiments, a separate dielectric lining material 401 (e.g., a ceramic) may be included around the electrodes 406/408.

Figure 4C:
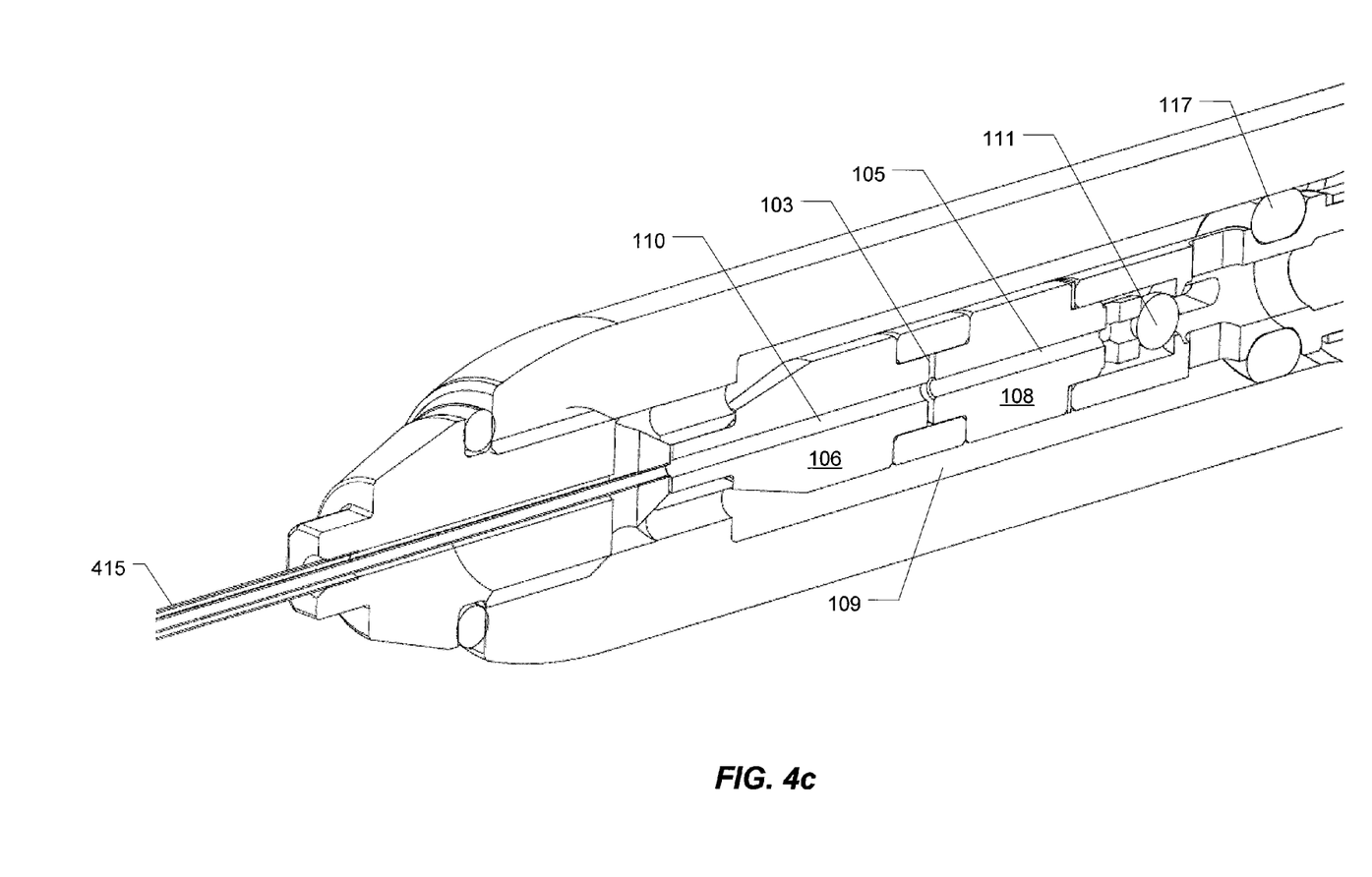

FIGS. 4b-c illustrate an alternate embodiment in which the fluid flows through the pulse chamber 403 and the flooded engine compartment 409 do not enter a merge chamber, but remain separate until the flows exit the tip into the eye. In this embodiment, the temperature of the flow leaving the pulse chamber 403 (e.g., through the central part of a dual lumen tip 415 may remain higher than the temperature of the flow leaving the flooded engine compartment (e.g., through an annulus of the dual lumen tip 415). FIG. 4c illustrates an isometric cut-away view of embodiment shown in FIG. 4b. Various other configurations are also possible that include a pulsed fluid pathway combining with and driving a cooler irrigation pathway.

Figure 5:
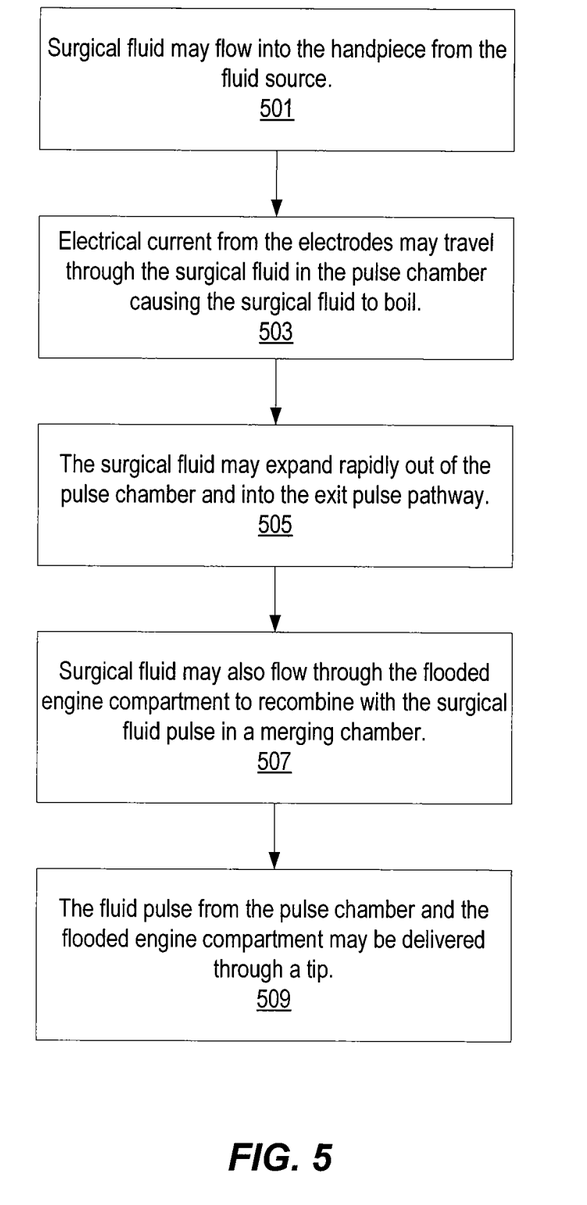
FIG. 5 illustrates a flowchart of fluid flow through the handpiece, according to an embodiment.

FIG. 5 illustrates a flowchart of an embodiment of fluid flow through the handpiece. The elements provided in the flowchart are illustrative only. Various provided elements may be omitted, additional elements may be added, and/or various elements may be performed in a different order than provided below.

At 501, surgical fluid may flow into the handpiece 101 from the fluid source 115. Surgical fluid may flow through the check valve 111 into the pulse chamber 103 and through the exit pulse pathway 110 into the pulse chamber 103 to prime the pulse chamber 103.

At 503, electrical current from the electrodes 106 and 108 may travel through the surgical fluid in the pulse chamber 103 causing the surgical fluid to boil.

At 505, the surgical fluid may expand rapidly out of the pulse chamber 103 and into the exit pulse pathway 110.

At 507, surgical fluid from the fluid source 115 may also flow through the flooded engine compartment 109 and through the irrigation pathway 107 to recombine with the surgical fluid pulse (exiting from the pulse chamber 103) in a merging chamber 112 that joins the irrigation pathway 107 and the exit pulse pathway 110. In some embodiments, the flows may not recombine in the merging chamber 112 (e.g., the flows may recombine in the eye after separately exiting a separate lumen in a dual lumen tip).

At 509, the fluid pulse from the pulse chamber 103 and the fluid from the flooded engine compartment 109 may be delivered through a tip 104 (which may be, for example, a single lumen tip or a dual lumen tip). In some embodiments, the single lumen tip may provide both irrigation and fluidic pulses simultaneously through the same fluid pathway.

Figure 6:
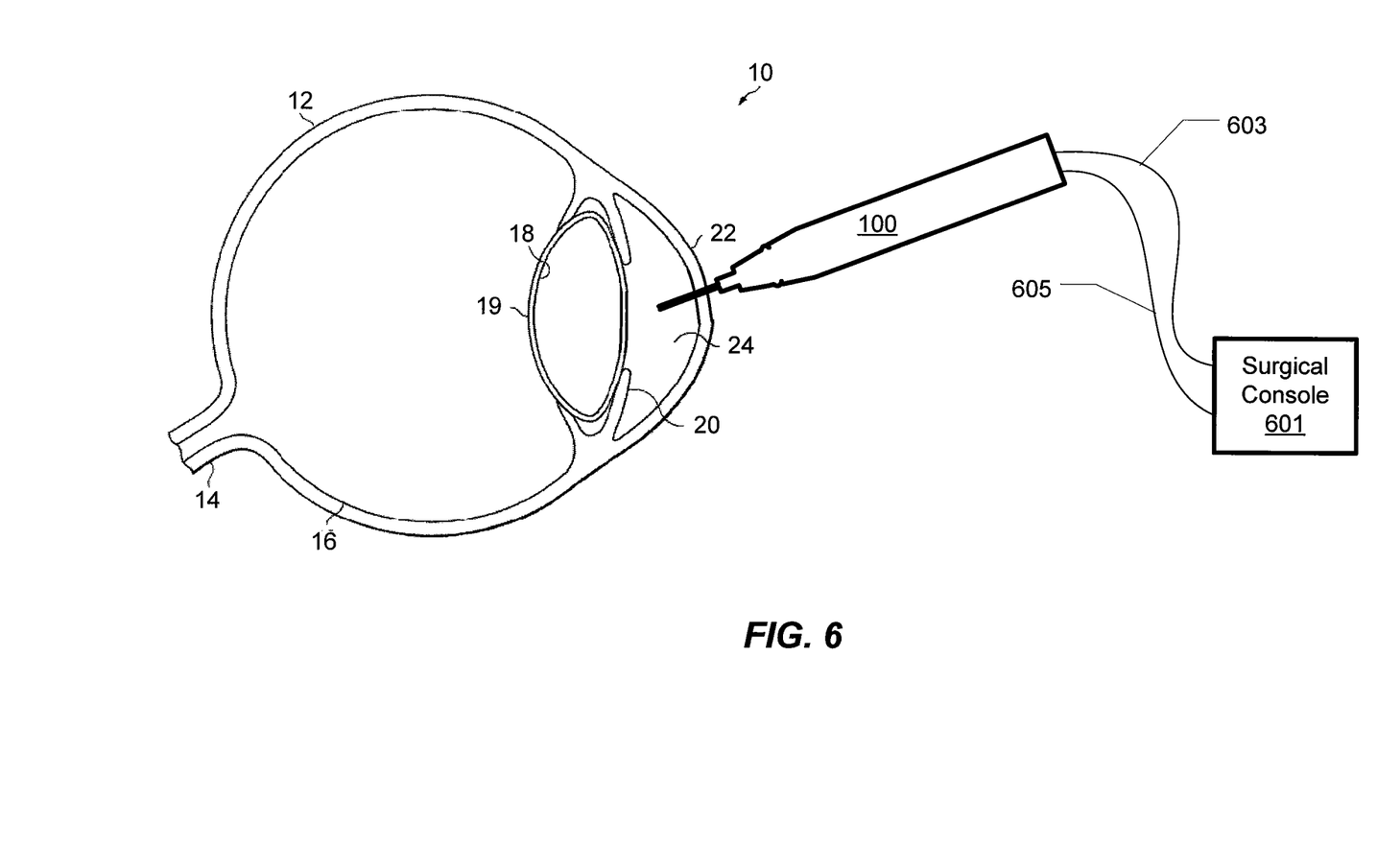
FIG. 6 illustrates a handpiece coupled to a surgical console, according to an embodiment.

FIG. 6 illustrates a cross sectional view of eye 10 and handpiece 100 (FIG. 6 is not to scale). As noted above, the handpiece 100 may be used for cataract extraction. Eye 10 includes sclera 12, optic nerve 14, retina 16, lens 18, capsular bag 19, iris 20, cornea 22, and pupil 24. Lens 18 may focus light passing through cornea 22 and pupil 24 on to retina 16. Retina 16 may convert light to nerve impulses which retina 16 sends along optic nerve 14 to the brain. Iris 20 may regulate the amount of light passing through pupil 24 and lens 18 thereby allowing eye 10 to adapt to varying levels of light. Capsular bag 19 may hold lens 18 in place and may be transparent so that light may pass through it. Thus, the nerve impulses traveling along optic nerve 14 correspond to scenes visible to eye 10. If the lens becomes clouded, the lens 18 may be removed through injection of pulsed surgical fluid from the tip of handpiece 100. Handpiece 100 may be coupled to a surgical console 601 through one or more lines (e.g., fluid line 603, power line 605, etc).

Various modifications may be made to the presented embodiments by a person of ordinary skill in the art. Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A handpiece, comprising:
   a handpiece body;
   a pulse chamber configured to receive fluid from a fluid inlet port, wherein the pulse chamber is located in the handpiece body and at least partially bounded by a pair of electrodes, wherein the electrodes are configured to deliver a current to a fluid in the pulse chamber to cause the fluid to boil and exit the pulse chamber;
   a flooded engine compartment configured to receive fluid from the fluid inlet port; and
   a tip, fluidly coupled to the pulse chamber and the flooded engine compartment and configured to direct the fluid from the pulse chamber and the flooded engine compartment out of the handpiece;
   a merging chamber configured to receive heated fluid from the pulse chamber and fluid from the flooded engine compartment;
   wherein the tip is coupled to the merging chamber, wherein the tip is configured to direct the fluid received in the merging chamber out of the handpiece body.

2. The handpiece of claim 1,
   wherein the tip is a single lumen tip.

3. The handpiece of claim 1, wherein the heated fluid from the pulse chamber and the fluid from the flooded engine compartment mix in the merging chamber such that a temperature of the mixed fluid is between a temperature of the heated fluid from the pulse chamber and a temperature of the fluid from the flooded engine compartment.

4. The handpiece of claim 1, wherein fluid is capable of flowing through the flooded engine compartment, the merging chamber, and then into the pulse chamber during an initial priming process before current is directed to fluid in the pulse chamber.

5. The handpiece of claim 1, wherein the flooded engine compartment is in thermal contact with the pulse chamber such that fluid in the flooded engine compartment receives heat from the pulse chamber.

6. The handpiece of claim 1, further comprising a check valve, wherein the check valve is configured to inhibit fluid flow from the pulse chamber toward the fluid inlet port.

7. The handpiece of claim 6, wherein the check valve is configured to be wetted by fluid flow from the fluid inlet port to the flooded engine compartment such that if the check valve were stuck due to a salt bond, the check valve would become unstuck via the wetting.

8. The handpiece of claim 1, wherein the flooded engine compartment surrounds the exterior of the pulse chamber.

9. The handpiece of claim 1, wherein the tip is configured to simultaneously provide the heated pulses and irrigation fluid.

10. An ophthalmic handpiece configured to direct heated pulses at a lens to liquefy the lens for removal from an eye, comprising:
    a handpiece body configured to receive fluid through a fluid inlet port from a surgical console;
    a pulse chamber configured to receive fluid from the fluid inlet port, wherein the pulse chamber is located in the handpiece body and at least partially bounded by a pair of electrodes, wherein the electrodes are configured to deliver a current to a fluid in the pulse chamber to cause the fluid to boil and exit the pulse chamber;
    a check valve, wherein the check valve is configured to inhibit fluid flow from the pulse chamber toward the fluid inlet port;
    a flooded engine compartment configured to receive fluid from the fluid inlet port; and
    a tip, fluidly coupled to the pulse chamber and the flooded engine compartment and configured to direct the fluid from the pulse chamber and the flooded engine compartment out of the handpiece;
    a merging chamber configured to receive heated fluid from the pulse chamber and fluid from the flooded engine compartment, wherein the heated fluid from the pulse chamber and the fluid from the flooded engine compartment mix in the merging chamber such that a temperature of the mixed fluid is between a temperature of the heated fluid from the pulse chamber and a temperature of the fluid from the flooded engine compartment; and
    wherein the tip is coupled to the merging chamber, wherein the tip is configured to provide the mixed fluid to a lens to liquefy the lens for removal from the eye.

11. The handpiece of claim 10,
    wherein the tip is a single lumen tip coupled to the merging chamber.

12. The handpiece of claim 10, wherein fluid is capable of flowing through the flooded engine compartment, the merging chamber, and then into the pulse chamber during an initial priming process before current is directed to fluid in the pulse chamber.

13. The handpiece of claim 10, wherein the tip is a dual lumen tip.

14. The handpiece of claim 10, wherein the flooded engine compartment is in thermal contact with the pulse chamber such that fluid in the flooded engine compartment receives heat from the pulse chamber.

15. The handpiece of claim 10, wherein the check valve is configured to be wetted by fluid flow from the fluid inlet port to the flooded engine compartment such that if the check valve were stuck due to a salt bond, the check valve would become unstuck via the wetting.

16. The handpiece of claim 10, wherein the flooded engine compartment surrounds the exterior of the pulse chamber.

* * * * *